US012741011B2

(12) United States Patent
Moon et al.

(10) Patent No.: US 12,741,011 B2
(45) Date of Patent: Sep. 22, 2026

(54) LIQUID FORMULATION

(71) Applicant: HANMI PHARM. CO., LTD., Hwaseong-si (KR)

(72) Inventors: Ji Hye Moon, Hwaseong-si (KR); Ji Eun Lee, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 975 days.

(21) Appl. No.: 17/927,257

(22) PCT Filed: May 24, 2021

(86) PCT No.: PCT/KR2021/006461
§ 371 (c)(1),
(2) Date: Nov. 22, 2022

(87) PCT Pub. No.: WO2021/235915
PCT Pub. Date: Nov. 25, 2021

(65) Prior Publication Data

US 2023/0210949 A1 Jul. 6, 2023

(30) Foreign Application Priority Data

May 22, 2020 (KR) ........................ 10-2020-0061879

(51) Int. Cl.

| | |
|---|---|
| ***A61K 38/17*** | (2006.01) |
| ***A61K 9/08*** | (2006.01) |
| ***A61K 47/18*** | (2017.01) |
| ***A61K 47/20*** | (2006.01) |
| ***A61K 47/26*** | (2006.01) |
| ***A61K 47/64*** | (2017.01) |
| ***A61K 47/68*** | (2017.01) |

(52) U.S. Cl.
CPC ............ *A61K 38/1796* (2013.01); *A61K 9/08* (2013.01); *A61K 47/183* (2013.01); *A61K 47/20* (2013.01); *A61K 47/26* (2013.01); *A61K 47/64* (2017.08); *A61K 47/68* (2017.08)

(58) Field of Classification Search
None
See application file for complete search history.

(56) References Cited

U.S. PATENT DOCUMENTS

| | | | | |
|---|---|---|---|---|
| 9,731,031 | B2 * | 8/2017 | Jung .................. | A61K 47/6811 |
| 2009/0186819 | A1 | 7/2009 | Carrier et al. | |
| 2009/0226530 | A1 * | 9/2009 | Lassner .................. | A61P 25/04 424/490 |

FOREIGN PATENT DOCUMENTS

| | | | |
|---|---|---|---|
| CN | 102026666 | A | 4/2011 |
| CN | 104519904 | A | 4/2015 |
| CN | 109071624 | A | 12/2018 |
| KR | 10-0725315 | B1 | 5/2007 |
| KR | 10-0925017 | B1 | 10/2009 |
| KR | 10-2012-0139579 | A | 12/2012 |
| KR | 10-2014-0098607 | A | 8/2014 |
| WO | 2010/016940 | A2 | 2/2010 |
| WO | 2014/073842 | A1 | 5/2014 |
| WO | 2015/200324 | A1 | 12/2015 |
| WO | 2019/171352 | A2 | 9/2019 |

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25. (Year: 2002).*
International Search Report for PCT/KR2021/006461 dated Sep. 27, 2021 [PCT/ISA/210].
Extended European Search Report issued Jan. 8, 2025 in European Application No. 21807569.5.
Anonymous: "Efinopegdutide", Registry, Chemical Abstracts Service, Columbus, Ohio, US, Jan. 8, 2017, XP002793492, pp. 1-3.

* cited by examiner

*Primary Examiner* — Vanessa L. Ford
*Assistant Examiner* — Sandra Carter
(74) *Attorney, Agent, or Firm* — Sughrue Mion, PLLC

(57) ABSTRACT

A liquid formulation of a long-acting conjugate of a peptide having activities for a glucagon receptor and a GLP-1 receptor, and a method for preparing the liquid formulation are disclosed. The liquid formulation contains 18 nmol/mL to 940 nmol/mL of the long-acting conjugate, a buffering agent in an amount for maintaining the pH of the liquid formulation in the range of 4.5 to 7.5, and 1% (w/v) to 20% (w/v) of saccharide, and 0.001% (w/v) to 0.2% (w/v) of a nonionic surfactant.

17 Claims, No Drawings

Specification includes a Sequence Listing.

LIQUID FORMULATION

CROSS REFERENCE TO RELATED APPLICATIONS

This application is a National Stage of International Application No. PCT/KR2021/006461 filed May 24, 2021, claiming priority based on Korea Patent Application No. 10-2020-0061879 filed May 22, 2020.

INCORPORATION BY REFERENCE OF SEQUENCE LISTING

The content of the electronically submitted sequence listing, file name: Q269659_Sequence_Listing_As_Filed.txt; size: 12,918 bytes; and date of creation: Nov. 21, 2022, filed herewith, is incorporated herein by reference in its entirety.

TECHNICAL FIELD

The present invention relates to a liquid formulation of a long-acting conjugate of a peptide having activities for a glucagon receptor and a GLP-1 receptor, and a method of preparing the liquid formulation.

BACKGROUND ART

Due to recent economic growth and changes in dietary habits, etc., the incidence of metabolic syndrome-associated diseases including various diseases such as obesity, hyperlipidemia, hypertension, arteriosclerosis, hyperinsulinemia, diabetes, or liver diseases is rapidly increasing. These diseases may occur independently, but in general, they mostly occur in a close relationship with each other, being accompanied by various symptoms. According to the World Health Organization (WHO), more than one billion adults are overweight worldwide, among them over three million are clinically diagnosed with obesity, and in particular, 250,000 people in Europe, and more than 2.5 million people worldwide die of overweight- or obesity-related diseases every year. Obesity is recognized as a serious disease which is prevalent across the world and is a cause of various diseases, but it is believed that it can be overcome by self-reliant efforts. However, obesity is not readily curable, because it is a complex disease associated with the mechanisms of appetite control and energy metabolism. Accordingly, the treatment of obesity requires not only the patient's own efforts, but also a method capable of treating abnormal mechanisms associated with appetite control and energy metabolism. Thus, constant efforts have been made to develop drugs for treating the abnormal mechanisms.

As a result of these efforts, anti-obesity drugs such as RIMONABANT® (SANOFI-AVENTIS), SIBUTRAMINE® (ABBOTT), CONTRAVE® (TAKEDA), ORLISTAT® (ROCHE), etc. have been developed, but they have the disadvantages of serious adverse effects or very weak anti-obesity effects. Accordingly, many extensive studies have been made to develop novel therapeutic agents for obesity which can solve the problems of the conventional anti-obesity drugs. Recently, much attention has been focused on oxyntomodulin, which has activities for all of GLP-1 receptors and glucagon receptors. Oxyntomodulin is a peptide produced from a glucagon precursor, pre-glucagon, and shows potency as an anti-obesity therapeutic agent because it inhibits food intake like GLP-1, promotes satiety, and has a lipolytic activity like glucagon.

Based on the dual function of the oxyntomodulin peptide, it has been actively studied as a drug for the treatment of obesity. For example, Korean Patent No. 925017 discloses a pharmaceutical composition including oxyntomodulin as an active ingredient for the treatment of overweight human, which is administered via an oral, parenteral, mucosal, rectal, subcutaneous, or transdermal route. However, it has been reported that this anti-obesity drug including oxyntomodulin has a short in vivo half-life and weak therapeutic efficacy, even when administered at a high dose three times a day. Thus, many efforts have been made to improve the in vivo half-life or therapeutic effect of oxyntomodulin on obesity by its modification. Meanwhile, the previously developed oxyntomodulin or derivatives thereof still have two major disadvantages in that they have to be administered daily due to a short half-life and low efficacy, and that an excessive amount of the drug must be administered.

DISCLOSURE

Technical Problem

It is necessary to maintain the pharmaceutical efficacy of the drug in vivo while restraining physicochemical changes of the drug during long-term storage by adding a stabilizer to a protein or a peptide in a solution state.

Technical Solution

It is one object of the present invention to provide a liquid formulation of a long-acting conjugate of a peptide having activities for a glucagon receptor and a GLP-1 (Glucagon-like peptide-1) receptor, in which a peptide having activities for a glucagon receptor and a GLP-1 receptor, and an immunoglobulin Fc fragment are linked.

It is another object of the present invention to provide a method for preparing a liquid formulation of a long-acting conjugate of a peptide having activities for a glucagon receptor and a GLP-1 receptor.

Advantageous Effects

The liquid formulation of a long-acting conjugate of a peptide having activities for a glucagon receptor and a GLP-1 receptor is a novel composition characterized by the presence of a saccharide and no sugar alcohol, and provides excellent effects in stress and/or accelerated tests that determine the stability of drugs as well as long-term storage stability, and thus can be used as a novel liquid formulation that can be stored stably without decomposition of the drug. In addition, since the liquid formulation of the present invention has an osmotic pressure range similar to that of blood, it does not cause pain when administered to a patient, thereby improving patient administration convenience.

DETAILED DESCRIPTION OF THE INVENTION

One aspect for implementing the present invention provides a liquid formulation of a long-acting conjugate of a peptide having activities for a glucagon receptor and a GLP-1 (Glucagon-like peptide-1) receptor, in which a peptide having activities for a glucagon receptor and a GLP-1 receptor, and an immunoglobulin Fc fragment are linked. The long-acting conjugate may refer to a substance in which a peptide having activities for a glucagon receptor and a GLP-1 receptor is covalently bonded to an immunoglobulin Fc fragment by a linker.

In one embodiment, the liquid formulation is a liquid formulation of a peptide conjugate including the peptide conjugate of Chemical Formula 1 below; a buffering agent; a saccharide; and a nonionic surfactant:

[Chemical Formula 1]

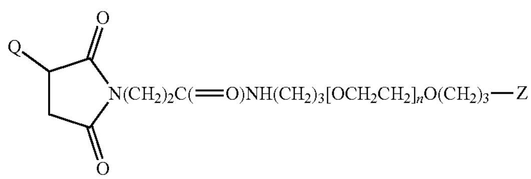

In Chemical Formula 1 above,

Q is a peptide of General Formula 1 below;

Z is an immunoglobulin Fc fragment; and n is a natural number, wherein the value of n is determined such that the average molecular weight of the $[OCH_2CH_2]n$ region in the peptide conjugate is 10 kDa:

```
[General Formula 1]
                                        (SEQ ID NO: 1)
His-Xaa2-Gln-Gly-Thr-Phe-Thr-Ser-Asp-Tyr-Ser-

Xaa12-Tyr-Leu-Asp-Xaa16-Lys-Arg-Ala-Xaa20-Glu-

Phe-Val-Gln-Trp-Leu-Met-Asn-Thr-Cys,
```

In General Formula 1 above,

Xaa2 is 2-aminoisobutyric acid (Aib), Xaa12 is lysine (K), Xaa16 is glutamic acid (E), Xaa20 is lysine (K); and a lactam ring may or may not be formed between Xaa12 and Xaa16 or Xaa16 and Xaa20 residues.

In the liquid formulation according to any one of the preceding embodiments, the liquid formulation is characterized in that it that is a liquid formulation of a peptide conjugate including 18 nmol/mL to 940 nmol/mL of a peptide conjugate of Chemical Formula 1 below; a buffering agent in an amount for maintaining the pH of the liquid formulation in the range of 4.5 to 7.5; 1% (w/v) to 20% (w/v) of a saccharide; and 0.001% (w/v) to 0.2% (w/v) of a nonionic surfactant.

In the liquid formulation according to any one of the preceding embodiments, the peptide is characterized in that it that includes an amino acid sequence of SEQ ID NOS: 2, 3 or 4.

In the liquid formulation according to any one of the preceding embodiments, the Q is characterized in that it that includes an amino acid sequence of SEQ ID NO: 3.

In the liquid formulation according to any one of the preceding embodiments, the Q is characterized in that it that is amidated at the C-terminus thereof.

In the liquid formulation according to any one of the preceding embodiments, the Q is characterized in that it that is linked via a sulfur atom of cysteine in the peptide.

In the liquid formulation according to any one of the preceding embodiments, the immunoglobulin Fc fragment is characterized in that it that is derived from IgG4.

In the liquid formulation according to any one of the preceding embodiments, the Z is characterized in that it that is a structure in which two polypeptide chains are linked by a disulfide bond, and are linked only through a nitrogen atom in one of the two chains.

In the liquid formulation according to any one of the preceding embodiments, the Z is characterized in that it that includes a monomer of the amino acid sequence of SEQ ID NO: 5.

In the liquid formulation according to any one of the preceding embodiments, the Z is characterized in that it that is linked via a nitrogen atom of proline at the N-terminus thereof.

In the liquid formulation according to any one of the preceding embodiments, the immunoglobulin Fc fragment and Q are characterized in that it that is non-glycosylated.

In the liquid formulation according to any one of the preceding embodiments, the liquid formulation is characterized in that it that does not include a sugar alcohol.

In the liquid formulation according to any one of the preceding embodiments, the liquid formulation may or may not include an isotonic agent.

In the liquid formulation according to any one of the preceding embodiments, the buffering agent is characterized in that it that is selected from the group consisting of citric acid and a salt thereof, acetic acid and a salt thereof, histidine and a salt thereof, phosphoric acid and a salt thereof, and a combination thereof.

In the liquid formulation according to any one of the preceding embodiments, the buffering agent is characterized in that it that is acetic acid and a salt thereof.

In the liquid formulation according to any one of the preceding embodiments, the pH of the liquid formulation is characterized in that it that is 4.8 to 6.0.

In the liquid formulation according to any one of the preceding embodiments, the pH of the liquid formulation is characterized in that it that is 4.9 to 5.3.

In the liquid formulation according to any one of the preceding embodiments, the concentration of the buffering agent is characterized in that it that is 5 mM to 100 mM for maintaining the pH of the liquid formulation in the range of 4.5 to 7.5.

In the liquid formulation according to any one of the preceding embodiments, the saccharide is characterized in that it that is glucose, fructose, galactose, lactose, maltose, sucrose, or a combination thereof.

In the liquid formulation according to any one of the preceding embodiments, the saccharide is characterized in that it that is sucrose.

In the liquid formulation according to any one of the preceding embodiments, the saccharide is characterized in that it that is present in a concentration of 1% (w/v) to 20% (w/v) in the liquid formulation.

In the liquid formulation according to any one of the preceding embodiments, the nonionic surfactant is characterized in that it that is poloxamer, polysorbate, or a combination thereof.

In the liquid formulation according to any one of the preceding embodiments, the nonionic surfactant is characterized in that it that is selected from the group consisting of poloxamer 188, polysorbate 20, polysorbate 40, polysorbate 60, polysorbate 80, and a combination thereof.

In the liquid formulation according to any one of the preceding embodiments, the nonionic surfactant is characterized in that it that is present in a concentration of 0.001% (w/v) to 0.2% (w/v) in the liquid formulation.

In the liquid formulation according to any one of the preceding embodiments, the peptide conjugate of Chemical Formula 1 above is characterized in that it that is present in a concentration of 18 nmol/mL to 940 nmol/mL in the liquid formulation.

In the liquid formulation according to any one of the preceding embodiments, liquid formulation is characterized in that it that further includes a stabilizer selected from the group consisting of arginine, glycine, methionine, and a combination thereof.

In the liquid formulation according to any one of the preceding embodiments, the liquid formulation is characterized in that it that includes: the peptide conjugate of Chemical Formula 1; a buffering agent selected from citric acid and a salt thereof, acetic acid and a salt thereof, histidine and a salt thereof, phosphoric acid and a salt thereof, and a combination thereof; a saccharide selected from the group consisting of glucose, fructose, galactose, lactose, maltose, sucrose, or a combination thereof; and a nonionic surfactant selected from poloxamer, polysorbate, and a combination thereof, wherein the pH of the liquid formulation is 4.8 to 6.0.

In the liquid formulation according to any one of the preceding embodiments, the liquid formulation is characterized in that it that includes: the peptide conjugate of Chemical Formula 1; 5 mM to 100 mM of a buffering agent selected from citric acid and a salt thereof, acetic acid and a salt thereof, histidine and a salt thereof, phosphoric acid and a salt thereof, and a combination thereof for maintaining the pH of the liquid formulation in the range of 4.8 to 6.0; 1% (w/v) to 20% (w/v) of a saccharide selected from the group consisting of glucose, fructose, galactose, lactose, maltose, sucrose, or a combination thereof; and 0.001% (w/v) to 0.2% (w/v) of a nonionic surfactant selected from poloxamer, polysorbate, and a combination thereof.

In the liquid formulation according to any one of the preceding embodiments, the liquid formulation is characterized in that it that includes: the peptide conjugate of Chemical Formula 1; 5 mM to 100 mM of a buffering agent for maintaining the pH of the liquid formulation in the range of 4.8 to 6.0; 1% (w/v) to 20% (w/v) of sucrose; and 0.001% (w/v) to 0.2% (w/v) of polysorbate.

In the liquid formulation according to any one of the preceding embodiments, the immunoglobulin Fc region is characterized in that it that is an IgG-, IgA-, IgD-, IgE-, or IgM-derived Fc fragment.

In the liquid formulation according to any one of the preceding embodiments, the immunoglobulin Fc region is characterized in that it that is selected from the group consisting of (a) CH1 domain, CH2 domain, CH3 domain, and CH4 domain; (b) CH1 domain and CH2 domain; (c) CH1 domain and CH3 domain; (d) CH2 domain and CH3 domain; (e) a combination between one or two or more domains among CH1 domain, CH2 domain, CH3 domain and CH4 domain, and an immunoglobulin hinge region or a part of the hinge region), and (f) a dimer between each domain of the heavy chain constant region and the light chain constant region.

In the liquid formulation according to any one of the preceding embodiments, each domain of the immunoglobulin Fc fragment is characterized in that it that is a hybrid of domains having different origins derived from an immunoglobulin selected from the group consisting of IgG, IgA, IgD, IgE, and IgM.

In the liquid formulation according to any one of the preceding embodiments, the immunoglobulin Fc fragment is characterized in that it that is in the form of a dimer or multimer, composed of a single-chain immunoglobulin consisting of domains of the same origin.

In the liquid formulation according to any one of the preceding embodiments, the immunoglobulin Fc fragment is characterized in that it that is an IgG4 Fc fragment.

In the liquid formulation according to any one of the preceding embodiments, the immunoglobulin Fc fragment is characterized in that it that is a human aglycosylated IgG4 Fc fragment.

In the liquid formulation according to any one of the preceding embodiments, the immunoglobulin Fc fragment is characterized in that it that is a native Fc derivative, including: a modification where the site capable of forming an inter-disulfide bond is removed; a modification where several N-terminal amino acids from native Fc are removed; a modification where a methionine residue is added to the N-terminus of native Fc; a modification where complement binding sites are removed; a modification where antibody-dependent cell-mediated cytotoxicity (ADCC) sites are removed, or a combination thereof.

In the liquid formulation according to any one of the preceding embodiments, the liquid formulation is characterized in that it that includes: the peptide conjugate of Chemical Formula 1 including Q consisting of the amino acid sequence of SEQ ID NO: 2, 3, or 4; 5 mM to 100 mM of a buffering agent selected from citric acid and a salt thereof, acetic acid and a salt thereof, histidine and a salt thereof, phosphoric acid and a salt thereof, and a combination thereof for maintaining the pH of the liquid formulation in the range of 4.8 to 6.0; 1% (w/v) to 20% (w/v) of a saccharide selected from the group consisting of glucose, fructose, galactose, lactose, maltose, sucrose, or a combination thereof; and 0.001% (w/v) to 0.2% (w/v) of a nonionic surfactant selected from poloxamer, polysorbate, and a combination thereof.

In the liquid formulation according to any one of the preceding embodiments, the liquid formulation is characterized in that it that includes: the peptide conjugate of Chemical Formula 1 including Q consisting of the amino acid sequence of SEQ ID NO: 2, 3, or 4; 5 mM to 100 mM of a buffering agent selected from citric acid and a salt thereof, acetic acid and a salt thereof, histidine and a salt thereof, phosphoric acid and a salt thereof, and a combination thereof for maintaining the pH of the liquid formulation in the range of 4.8 to 6.0; 1% (w/v) to 20% (w/v) of sucrose; and 0.001% (w/v) to 0.2% (w/v) of a nonionic surfactant selected from poloxamer, polysorbate, and a combination thereof.

In the liquid formulation according to any one of the preceding embodiments, the liquid formulation is characterized in that it that includes: 93 nmol/mL to 565 nmol/mL of the peptide conjugate of Chemical Formula 1, in which Q having an amidated C-terminus is linked via a sulfur atom of cysteine; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 4% (w/v) to 10% (w/v) of a saccharide; and 0.01% (w/v) to 0.1% (w/v) of a nonionic surfactant selected from poloxamer, polysorbate, or a combination thereof.

In the liquid formulation according to any one of the preceding embodiments, the liquid formulation is characterized in that it that includes: 93 nmol/mL to 565 nmol/mL of the peptide conjugate of Chemical Formula 1, in which Q having an amidated C-terminus is linked via a sulfur atom of cysteine and Z is linked via a nitrogen atom of proline at the N-terminus thereof; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 4% (w/v) to 10% (w/v) of a saccharide; and 0.01% (w/v) to 0.1% (w/v) of a nonionic surfactant selected from poloxamer, polysorbate, or a combination thereof.

In the liquid formulation according to any one of the preceding embodiments, the concentration of the peptide conjugate of Chemical Formula 1 above in the liquid formulation is characterized in that it that is 274 nmol/mL to 474 nmol/mL.

In the liquid formulation according to any one of the preceding embodiments, the concentration of the peptide conjugate of Chemical Formula 1 above in the liquid formulation is characterized in that it that is 320 nmol/mL to 430 nmol/mL.

In the liquid formulation according to any one of the preceding embodiments, the liquid formulation is characterized in that it that has a transparent appearance when stored for one week under stress test conditions of 40° C.±2° C. and relative humidity of 75%±5%.

Another aspect for implementing the present invention provides a method for preparing a liquid formulation of a peptide conjugate, which is the liquid formulation according to any one of the preceding embodiments, including: mixing (a) the peptide conjugate of Chemical Formula 1 with (b) i) a buffering agent, ii) a saccharide, and iii) a surfactant.

MODE FOR CARRYING OUT THE INVENTION

Hereinafter, the present invention will be described in more detail.

Meanwhile, each of the explanations and exemplary embodiments disclosed herein can be applied to each other explanation and exemplary embodiment. That is, all of the combinations of various factors disclosed herein belong to the scope of the present invention. Moreover, the scope of the present invention should not be limited by the specific disclosure provided hereinbelow.

Additionally, those of ordinary skill in the art may be able to recognize or confirm, using only conventional experimentation, many equivalents to the particular aspects of the invention described herein. Furthermore, it is also intended that these equivalents be included in the present invention.

Throughout the entire specification of the present invention, not only the conventional one-letter and three-letter codes for naturally occurring amino acids, but also those three-letter codes generally allowed for other amino acids, such as α-aminoisobutyric acid (Aib), etc. are used. Additionally, the amino acids mentioned herein are abbreviated according to the nomenclature rules of IUPAC-IUB as follows:

alanine Ala, A
arginine Arg, R
asparagine Asn, N
aspartic acid Asp, D
cysteine Cys, C
glutamic acid Glu, E
glutamine Gln, Q
glycine Gly, G
histidine His, H
isoleucine Ile, I
leucine Leu, L
lysine Lys, K
methionine Met, M
phenylalanine Phe, F
proline Pro, P
serine Ser, S
threonine Thr, T
tryptophan Trp, W
tyrosine Tyr, Y
valine Val, V One aspect for implementing the present invention provides a liquid formulation of a long-acting conjugate of a peptide having activities for a glucagon receptor and a GLP-1 (Glucagon-like peptide-1) receptor, in which a peptide having activities for a glucagon receptor and a GLP-1 receptor, and an immunoglobulin Fc fragment are linked.

Specifically, the present invention provides a liquid formulation including a peptide conjugate of Chemical Formula 1 below; a buffering agent; a saccharide; and a nonionic surfactant:

[Chemical Formula 1]

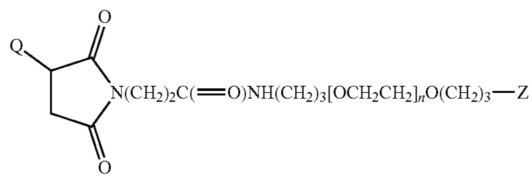

In Chemical Formula 1 above,

Q is a peptide of General Formula 1 below;

Z is an immunoglobulin Fc fragment; and n is a natural number, wherein the value of n is determined such that the average molecular weight of the $[OCH_2CH_2]_n$ region in the peptide conjugate is 10 kDa:

[General Formula 1] (SEQ ID NO: 1)

His-Xaa2-Gln-Gly-Thr-Phe-Thr-Ser-Asp-Tyr-Ser-Xaa12-Tyr-Leu-Asp-Xaa16-Lys-Arg-Ala-$Xaa_{20}$-Glu-Phe-Val-Gln-Trp-Leu-Met-Asn-Thr-Cys,

In General Formula 1 above,

Xaa2 is 2-aminoisobutyric acid (Aib), Xaa12 is lysine (K), Xaa16 is glutamic acid (E), Xaa20 is lysine (K); and a lactam ring may or may not be formed between Xaa12 and Xaa16 or Xaa16 and Xaa20 residues.

The peptide conjugate of Chemical Formula 1 has a structure in which the peptide Q of SEQ ID NO: 1 and a human immunoglobulin Fc fragment Z are covalently linked through an ethylene glycol repeating unit, wherein each Q may be linked to a succinimide ring of Chemical Formula 1, and Z may be linked to an oxypropylene group of Chemical Formula 1.

The Q of the peptide conjugate may be a peptide having activities for a glucagon receptor and a GLP-1 receptor.

In one embodiment, the moiety at which Q is linked to the succinimide ring of Chemical Formula 1 may be a sulfur atom of the C-terminal cysteine of Q.

The Z is an human immunoglobulin Fc fragment, and the immunoglobulin Fc region in the present specification encompasses not only a native sequence obtained from papain digestion of an immunoglobulin, but also derivatives thereof, for example, sequences in which one or more amino acid residues in the native sequence are converted by deletion, insertion, non-conservative or conservative substitution, or a combination thereof, and thus the sequences become different from the native sequence, etc.

The moiety linked to the oxypropylene group in Z is not specifically limited. In one embodiment of the present invention, the moiety of Z linked to the oxypropylene group may be an N-terminal nitrogen or a nitrogen atom of a residue in Z (e.g., epsilon nitrogen of lysine). In one specific embodiment of the present invention, the moiety where Z is linked to the oxypropylene group of Chemical Formula 1 may be the N-terminal proline of Z.

The Z may have a structure in which two polypeptide chains are linked by an inter-disulfide bond, or a structure in which two polypeptide chains are linked through a nitrogen atom in only one of the two chains, but is not limited thereto. The linkage through the nitrogen atom may be linked to the epsilon amino atom or the N-terminal amino group of lysine via reductive amination.

The reductive amination reaction refers to a reaction in which an amine group or amino group of a reactant reacts with an aldehyde of another reactant (i.e., a functional group capable of reductive amination) to produce an amine, and an amine bond is formed by a reduction reaction thereafter. The reductive amination reaction is a reaction of organic synthesis widely known in the art.

In one embodiment, the Z may be linked through a nitrogen atom of the N-terminal proline thereof, but is not limited thereto.

In one embodiment, the immunoglobulin Fc fragment and Q may be aglycosylated, but is not limited thereto. In the present invention, the peptide conjugate of Chemical Formula 1 above is referred to as "long-acting conjugate". In the present invention, the long-acting conjugate may be used interchangeably with "long-acting oxyntomodulin derivative conjugate" or "peptide conjugate".

As used herein, the term "liquid formulation" refers to a drug formulated into a liquid form and is intended to include all liquid formulations for internal use and formulations for external use.

The liquid formulation of the present invention includes the peptide conjugate of Chemical Formula 1 showing a pharmacological effect, and a substance capable of stably maintaining and/or storing the peptide conjugate showing the pharmacological effect for a certain period of time when it is formulated in a liquid form.

In the liquid formulation of the peptide conjugate of Chemical Formula 1 of the present invention, storage stability is important for ensuring accurate dosage.

The liquid formulation may include a buffering agent, a saccharide, and a nonionic surfactant. Such a liquid formulation may be a solution formulation capable of stably storing a long-acting conjugate of a peptide having activities for a glucagon receptor and a GLP-1 receptor.

Additionally, the liquid formulation may further include a stabilizer, which is an amino acid selected from the group consisting of arginine, glycine, methionine, and a combination thereof, but is not limited thereto.

For example, the liquid formulation may essentially include a buffering agent, a saccharide, and a nonionic surfactant as the composition of the liquid formulation in addition to the peptide conjugate of Chemical Formula 1, which exhibits a pharmacological effect, or it may essentially include a buffering agent, a saccharide and a nonionic surfactant, and an amino acid stabilizer as an additional component, but is not particularly limited thereto. The present inventors surprisingly found that the composition of the peptide liquid formulation shows excellent stability without an amino acid stabilizer when the sugar alcohol is replaced by a saccharide, compared to a conventional formulation containing a buffering agent, a sugar alcohol, a nonionic surfactant, and an amino acid. Further, in the case of a formulation of the prior art containing a buffering agent, a sugar alcohol, a nonionic surfactant, and an amino acid, there was a problem that the osmotic pressure of the formulation was higher than that of blood at the concentration of ingredients that can ensure the stability of the formulation. In contrast, the formulation of the present invention has the advantages that the osmotic pressure can be lowered to a level similar to that of blood, and that the stability can be at least equal to or improved compared to the formulation of the prior art. Specifically, the above-described stability and osmotic pressure similar to that of blood can be realized by changing the sugar alcohol to a saccharide and partially adjusting the pH from the formulation of the prior art.

In general, in the case of blood, the osmotic pressure is about 300 mOsm/kg. The formulation of the present invention may have a range similar to the osmotic pressure of the blood, e.g., 300 mOsm/kg±50 mOsm/kg. As described above, the formulation of the present invention having an osmotic pressure similar to that of blood does not cause pain when administered to a patient, thereby improving administration convenience.

Meanwhile, in the case of methionine, an amino acid that may be additionally included in the formulation of the present invention, the presence or absence of methionine does not affect stability, so it may be excluded.

According to one specific embodiment of the present invention, the liquid formulation can stably maintain the above-mentioned long-acting conjugate even for up to 12 months, so it has excellent long-term stability and excellent residual rate up to 6 months even under accelerated conditions, and maintains a transparent appearance until week 4 under stress conditions.

In one embodiment, the liquid formulation of the present invention may not include a sugar alcohol.

In one embodiment, the liquid formulation of the present invention may or may not include an isotonic agent. For example, the liquid formulation of the present invention may not include sodium chloride, sodium sulfate, or sodium citrate, but is not limited thereto.

The isotonic agent refers to a substance that can control osmotic pressure. The isotonic agent may serve to properly maintain osmotic pressure when the liquid formulation according to the present invention is administered to the body.

Representative examples of the isotonic agent may include sodium chloride, sodium sulfate, or sodium citrate as a water-soluble inorganic salt, specifically sodium chloride, but is not particularly limited thereto.

The concentration of the isotonic agent in the liquid formulation according to the present invention may be 0 mM to 200 mM, 0 mM to 150 mM, 0 mM to 100 mM, 10 mM to 200 mM, 10 mM to 150 mM, 10 mM to 100 mM, 10 mM to 50 mM, 20 mM to 100 mM, 20 mM to 80 mM, 20 mM to 50 mM, 20 mM to 30 mM, or 40 mM to 50 mM, but is not particularly limited thereto. Such an isotonic agent may be an optional component additionally included in the above-described liquid formulation, and is not particularly limited thereto.

In particular, it is obvious that all of the contents described below apply to the type, concentration, or pH of each component constituting the liquid formulation.

The buffering agent, which is one component included in the liquid formulation of the present invention, can maintain the pH of a solution so that the pH of the liquid formulation does not rapidly change so as to make the peptide conjugate of Chemical Formula 1 stable. The buffering agent may also be referred to as a buffer system, and the buffering agent or buffer system serves to maintain the pH of the liquid formulation. Any buffering agent capable of maintaining a pH that can stabilize the peptide conjugate of Chemical Formula 1, which is the target material for stabilization, may be used without limitation.

The buffering agent may be a pH buffer, including phosphoric acid and a conjugate alkali salt thereof (e.g., phosphate: sodium phosphate, potassium phosphate, or a hydrogen or dihydrogen salt thereof), citric acid and a salt thereof (e.g., sodium citrate), acetic acid and a salt thereof (e.g., sodium acetate), or histidine and a salt thereof, and a mixture of these buffers may also be used, but the buffering agent is not limited thereto.

The liquid formulation of the present invention may include a buffer solution containing the buffering agent as a solvent of the liquid formulation, and specifically, the buffer solution may be selected from the group consisting of a citrate buffer solution (e.g., a sodium citrate buffer solution), an acetate buffer solution (e.g., a sodium acetate buffer solution), a phosphate buffer solution (e.g., a sodium phosphate buffer solution), a histidine buffer solution, and a combination thereof. Additionally, the buffer solution or the buffering agent in the liquid formulation (citric acid and a salt thereof, acetic acid and a salt thereof, histidine and a salt thereof, phosphoric acid and a salt thereof, or a combination thereof) may be contained in a concentration sufficient to maintain a target pH of the liquid formulation.

The pH of the liquid formulation may be in the range of about 4.5 to about 7.5, for example, about 4.5 to about 7.0, about 4.5 to about 6.5, about 4.5 to about 6.3, about 4.5 to about 6.0, about 4.5 to about 5.9, about 4.6 to about 5.8, about 4.7 to about 5.8, about 4.8 to about 6.0, about 4.8 to 5.8, about 4.8 to about 5.7, about 4.8 to 5.6, about 4.8 to about 5.5, about 4.8 to about 5.4, about 4.8 to about 5.3, about 4.9 to about 5.3, about 4.9 to about 5.2, about 5.0 to about 5.2, or about 5.1, but is not particularly limited thereto.

The concentration of the liquid formulation to reach the target pH may be about 1 mM to about 200 mM, more specifically about 5 mM to about 100 mM, about 5 mM to about 80 mM, about 5 mM to about 40 mM, about 8 mM to about 40 mM, about 5 mM to about 30 mM, or about 5 mM to about 25 mM, but is not particularly limited thereto.

The saccharide, which is one component included in the liquid formulation of the present invention, refers to monosaccharides, disaccharides, polysaccharides, oligosaccharides, etc., and can increase the stability of the long-acting conjugate of the peptide having activities for a glucagon receptor and a GLP-1 receptor. Specific examples may include monosaccharides such as mannose, glucose, fructose, galactose, fucose, and xylose; disaccharides such as lactose, maltose, and sucrose; and polysaccharides such as raffinose and dextran, but are not limited thereto.

The saccharide may be present in a concentration of about 1% (w/v) to about 20% (w/v), about 1% (w/v) to 15% (w/v), about 2% (w/v) to about 15% (w/v), about 2% (w/v) to about 12% (w/v), about 2% (w/v) to about 12% (w/v), about 3% (w/v) to about 10% (w/v), about 4% (w/v) to about 10% (w/v), about 5% (w/v) to about 10% (w/v), about 6% (w/v) to about 10% (w/v), about 7% (w/v) to about 10% (w/v), about 7% (w/v) to about 9% (w/v), about 8% (w/v) to about 9% (w/v), or about 8.5% (w/v) relative to the total solution of the liquid formulation, but is not particularly limited thereto.

Although not particularly limited thereto, the nonionic surfactant, which is one component included in the liquid formulation, lowers the surface tension of the protein solution, thereby preventing protein adsorption or aggregation on the hydrophobic surface.

Specific examples of the nonionic surfactant that can be used in the present invention may include polysorbates (e.g., polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate); the numerical value 20 after the polyoxyethylene group means the total number of oxyethylene groups $-(CH_2CH_2O)-$), poloxamer (PEO-PPO-PEO copolymer; PEO: poly(ethylene oxide), PPO: poly (propylene oxide)), polyethylene-polypropylene glycol, polyoxyethylene compounds (e.g., polyoxyethylene-stearate, polyoxyethylene alkyl ethers (alkyl: $C_1$-$C_{30}$), polyoxyethylene monoallyl ether, alkylphenyl polyoxyethylene copolymer (alkyl: $C_1$-$C_{30}$), etc.), sodium dodecyl sulfate (SDS), etc., or polysorbate or poloxamer. These may also be used alone or a combination of two or more thereof.

Specifically, the nonionic surfactant may be polysorbate 80, polysorbate 60, polysorbate 40, polysorbate 20, or poloxamer 188, and these may be used in combination, but is not particularly limited thereto.

In the present invention, it is preferable that the nonionic surfactant is not contained in a high concentration, and specifically, it may be contained in a concentration of about 0.2% (w/v) or less, for example, about 0.001% (w/v) to about 0.2% (w/v), about 0.001% (w/v) to about 0.1% (w/v), about 0.001% (w/v) to about 0.05% (w/v), about 0.005% (w/v) to about 0.08% (w/v), about 0.002% (w/v) to about 0.05% (w/v), about 0.005% (w/v) to about 0.05% (w/v), about 0.01% (w/v) to about 0.05% (w/v), about 0.01% (w/v) to about 0.04% (w/v), about 0.01% (w/v) to about 0.03% (w/v), or about 0.02% (w/v), but the concentration is not particularly limited thereto.

The amino acid, which is a type of stabilizer as an optional component that may be added to the liquid formulation, may be methionine, arginine, glycine, or a combination thereof, but is not limited thereto. In addition, the amino acid may be in the L-form, but is not particularly limited thereto.

The amino acid may inhibit the generation of impurities that may occur due to the oxidation reaction of the protein, but is not particularly limited thereto.

The amino acid may be present in a concentration of about 0.01 mg/mL to about 1 mg/mL, about 0.01 mg/mL to about 0.8 mg/mL, about 0.01 mg/mL to about 0.5 mg/mL, about 0.02 mg/mL to about 0.5 mg/mL, or about 0.02 mg/mL to about 0.4 mg/mL in the formulation, but is not particularly limited thereto.

Meanwhile, the liquid formulation of the present invention may optionally further include other components or materials known in the art within the range that does not impair the effects of the present invention, in addition to saccharide; buffering agent; and nonionic surfactant, which are essential components of the above-described liquid formulation; and amino acid, which is an optional component, but is not limited thereto.

The peptide conjugate of Chemical Formula 1 may be present in a pharmaceutically effective amount. For example, the concentration of the peptide conjugate of Chemical Formula 1 may be about 18 nmol/mL to about 940 nmol/mL, about 18.7 nmol/mL to about 935 nmol/mL about 18 nmol/mL to about 842 nmol/mL, about 18 nmol/mL to about 748 nmol/mL, about 18 nmol/mL to about 655 nmol/mL, about 18 nmol/mL to about 561 nmol/mL, about 18 nmol/mL to about 468 nmol/mL, about 18 nmol/mL to about 374 nmol/mL, about 93 nmol/mL to about 940 nmol/mL, about 93.5 nmol/mL to about 561 nmol/mL, about 93 nmol/mL to about 842 nmol/mL, about 93 nmol/mL to about 748 nmol/mL, about 93 nmol/mL to about 655 nmol/mL, about 93 nmol/mL to about 565 nmol/mL, about 93 nmol/mL to about 561 nmol/mL, about 93 nmol/mL to about 468 nmol/mL, about 150 nmol/mL to about 468 nmol/mL, about 200 nmol/mL to about 468 nmol/mL, about 250 nmol/mL to about 468 nmol/mL, about 274 nmol/mL to about 474 nmol/mL, about 280 nmol/mL to about 468 nmol/mL, about 300 nmol/mL to about 468 nmol/mL, about 300 nmol/mL to about 450 nmol/mL, about 320 nmol/mL to about 430 nmol/mL, about 320 nmol/mL to about 440 nmol/mL, about 340 nmol/mL to about 420 nmol/mL, about 340 nmol/mL to about 400 nmol/mL, about 350 nmol/mL to about 400 nmol/mL, about 360 nmol/mL to about 390 nmol/mL, about 365 nmol/mL to about 385 nmol/mL, about 370 nmol/mL to about 380 nmol/mL about 93 nmol/mL to about 374 nmol/mL, or about 374 nmol/mL, but is not limited thereto.

As used herein, the term "about" refers to a range which includes all of ±0.5, ±0.4, ±0.3, ±0.2, ±0.1, etc. and includes all of the values that are equivalent or similar to those following the values, but the range is not limited thereto.

In one embodiment, the liquid formulation may include the peptide conjugate of Chemical Formula 1; a buffering agent selected from citric acid and a salt thereof, acetic acid and a salt thereof, histidine and a salt thereof, phosphoric acid and a salt thereof, and a combination thereof; a saccharide selected from the group consisting of glucose, fructose, galactose, lactose, maltose, sucrose, or a combination thereof; and a nonionic surfactant selected from poloxamer, polysorbate, and a combination thereof, and the pH of the liquid formulation may be 4.8 to 6.0.

In one embodiment, the liquid formulation may include 18 nmol/mL to 940 nmol/mL of the peptide conjugate of Chemical Formula 1; 5 mM to 100 mM of a buffering agent selected from citric acid and a salt thereof, acetic acid and a salt thereof, histidine and a salt thereof, phosphoric acid and a salt thereof, and a combination thereof for maintaining the pH of the liquid formulation in the range of 4.8 to 6.0; 1% (w/v) to 20% (w/v) of a saccharide selected from the group consisting of glucose, fructose, galactose, lactose, maltose, sucrose, or a combination thereof; and 0.001% (w/v) to 0.2% (w/v) of a nonionic surfactant selected from poloxamer, polysorbate, and a combination thereof.

In one embodiment, the liquid formulation may include 18 nmol/mL to 940 nmol/mL of the peptide conjugate of Chemical Formula 1; 5 mM to 100 mM of acetic acid and a salt thereof for maintaining the pH of the liquid formulation in the range of 4.8% (w/v) to 6.0; 1% (w/v) to 20% (w/v) of sucrose; and 0.001% (w/v) to 0.2% (w/v) of polysorbate, but is not limited thereto.

In one embodiment, the liquid formulation may be a liquid formulation containing: 93 nmol/mL to 565 nmol/mL of the peptide conjugate of Chemical Formula 1, in which Q having an amidated C-terminus is linked via a sulfur atom of cysteine; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 4% (w/v) to 10% (w/v) of a saccharide; and 0.01% (w/v) to 0.1% (w/v) of a nonionic surfactant selected from poloxamer, polysorbate, or a combination thereof, but is not limited thereto.

The liquid formulation may have a transparent appearance when stored for one week under stress test conditions of 40° C.±2° C. and relative humidity of 75%±5%.

In one embodiment, the liquid formulation may have a transparent appearance when stored for about 1 week or more, about 2 weeks or more, about 3 weeks or more, about 4 weeks or more under stress test conditions of 40° C.±2° C. and relative humidity of 75%±5%.

According to an embodiment of the present invention, it was confirmed that the liquid formulation consisting of a buffering agent; a saccharide; and a nonionic surfactant, in addition to the peptide conjugate of Chemical Formula 1, has high stability for up to 6 months under accelerated conditions of 25° C.±2° C. and relative humidity of 60%±5% compared to the liquid formulation consisting of a buffering agent; a sugar alcohol; an amino acid; and a nonionic surfactant, and that the liquid formulation showed a transparent appearance when stored for one week under stress test conditions of 40° C.±2° C. and relative humidity of 75%±5%, and still showed transparent appearance even after 4 weeks (Tables 6 to 9).

As used herein, the term "accelerated testing" refers to a test designed to increase chemical degradation or physical change of a drug substance or drug product by adopting some excessive storage conditions of the official stability test of a drug product. In addition to the long-term stability test, the accelerated test evaluates chemical effects over a long period under non-accelerated conditions using accelerated test data and can evaluate the effects when conditions deviate from the indicated storage conditions for a short period of time, such as situations that may occur during transport. Additionally, it is a test designed to increase the rate of chemical degeneration or physical change of raw materials or drugs under excessive temperature or humidity conditions compared to normal storage conditions.

As used herein, the term "stress testing" refers to a test intended to identify the fundamental characteristics of the stability of a drug. It is carried out during drug development and is conducted under more stress conditions than accelerated tests, and it helps to identify expected degradation products and physical changes of the drug.

The Q of the peptide conjugate of Chemical Formula 1 may be a peptide having activities for a glucagon receptor and a GLP-1 (Glucagon-like peptide-1) receptor. The "peptide having activities for a glucagon receptor and a GLP-1 (Glucagon-like peptide-1) receptor" include various substances having a significant level of activities for a glucagon receptor and a GLP-1 receptor, such as various peptides.

Although it is not particularly limited thereto, the peptide having a significant level of activities for a glucagon receptor and a GLP-1 receptor may be used interchangeably with a "GCG/GLP-1 receptor dual agonist", "dual agonist", "oxyntomodulin derivative".

More specifically, the peptide having activities for a glucagon receptor and a GLP-1 receptor may be a peptide having activities for a glucagon receptor and a GLP-1 receptor including the sequence of General Formula 1 below:

```
[General Formula 1]
                                    (SEQ ID NO: 1)
His-Xaa2-Gln-Gly-Thr-Phe-Thr-Ser-Asp-Tyr-Ser-

Xaa12-Tyr-Leu-Asp-Xaa16-Lys-Arg-Ala-Xaa20-Glu-

Phe-Val-Gln-Trp-Leu-Met-Asn-Thr-Cys,
```

In General Formula 1 above,

Xaa2 is 2-aminoisobutyric acid (Aib), Xaa12 is lysine (K), Xaa16 is glutamic acid (E), Xaa20 is lysine (K); and a lactam ring may or may not be formed between Xaa12 and Xaa16 or Xaa16 and Xaa20 residues.

In the present specification, the "Aib" may be used interchangeably with "2-aminoisobutyric acid" or "aminoisobutyric acid", and 2-aminoisobutyric acid and aminoisobutyric acid may be used interchangeably with each other.

The peptide may include the amino acid sequence of SEQ ID NOS: 2, 3, or 4 or consist (essentially) of an amino acid sequence selected from the group consisting of SEQ ID NOS: 2, 3, or 4, but is not limited thereto.

Additionally, although described as "a peptide consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the peptide has an activity the same as or corresponding to that of the peptide which consists of an amino acid sequence of the corresponding SEQ ID NO, and even when the sequence addition or mutation is present, it obviously belongs to the scope of the present invention.

Meanwhile, the peptide may be non-naturally occurring.

The C-terminus of the peptide may be an amidated peptide or a peptide having a free carboxyl group (—COOH), or may include a peptide having an unmodified C-terminus, but is not limited thereto.

In one embodiment, the Q may be amidated at the C-terminus, but is not limited thereto.

In one embodiment, the Q may be non-glycosylated, but is not limited thereto.

Additionally, the peptide having activities for a glucagon receptor and a GLP-1 receptor may include an intramolecular bridge, e.g., a covalent bridge or a non-covalent bridge, and specifically may be in a form including a ring. A ring may be formed between the $12^{th}$ amino acid and the $16^{th}$ amino acid, or the $16^{th}$ amino acid and the $20^{th}$ amino acid, but is not particularly limited thereto. Non-limiting examples of the ring may include a lactam bridge (or lactam ring).

Further, the peptide according to the present invention may include all of those in the form of the peptide itself, a salt thereof (e.g., a pharmaceutically acceptable salt of the peptide), or a solvate thereof. Additionally, the peptide may be in any pharmaceutically acceptable form.

The kind of the salt is not particularly limited. However, the salt is preferably one that is safe and effective to a subject (e.g., a mammal), but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

As used herein, the term "solvate" refers to a complex formed between the peptide according to the present invention or a salt thereof and a solvent molecule.

As used herein, the term "peptide conjugate of Chemical Formula 1", being an active ingredient included in the liquid formulation of the present invention, may be included in the liquid formulation in a pharmacologically effective amount. Specifically, the conjugate is in a form, in which the peptide having activities for a glucagon receptor and a GLP-1 receptor, and an immunoglobulin Fc region are linked to each other by a linker, and may exhibit an enhanced duration of efficacy compared to a peptide having activities for a glucagon receptor and a GLP-1 receptor to which an immunoglobulin Fc region is not linked. In the present invention, such a conjugate is referred to as a "long-acting conjugate". In the present invention, the long-acting conjugate is used interchangeably with a "long-acting oxyntomodulin derivative conjugate" or "peptide conjugate".

Meanwhile, the conjugate may be non-naturally occurring.

Additionally, in the peptide conjugate of Chemical Formula 1, the linkage between Q, the peptide having activities for a glucagon receptor and a GLP-1 receptor, and the immunoglobulin Fc fragment may be achieved by a physical or chemical bond, a non-covalent or covalent bond, and specifically a covalent bond, but is not limited thereto.

Additionally, in the peptide conjugate of Chemical Formula 1, the method of linking Q, the peptide having activities for a glucagon receptor and a GLP-1 receptor, and the immunoglobulin Fc fragment is not particularly limited, but the peptide having activities for a glucagon receptor and a GLP-1 receptor, and the immunoglobulin Fc fragment may be linked to each other through a linker.

Specifically, the long-acting conjugate included in the liquid formulation of the present invention may be one represented by Chemical Formula 1 above.

The method for preparing the peptide conjugate is described in Korean Patent No. 10-725315, and the entire specification thereof is incorporated herein by reference.

As used herein, the term "immunoglobulin Fc fragment" refers to a heavy chain constant region excluding the heavy and light chain variable regions of an immunoglobulin. Specifically, the immunoglobulin Fc fragment may include the heavy chain constant region 2 (CH2) and/or heavy chain constant region 3 (CH3) portions, and more specifically may further include a hinge region (all or part of the hinge region).

The immunoglobulin Fc fragment may be a constitution constituting the moiety of the peptide conjugate of Chemical Formula 1 of the present invention. Specifically, it may correspond to Z in Chemical Formula 1 above.

Such an immunoglobulin Fc fragment may include a hinge region in the heavy chain constant region, but is not limited thereto.

In the present invention, the immunoglobulin Fc fragment may include a specific hinge sequence in the N-terminus.

As used herein, the term "hinge sequence" refers to a region which is located in the heavy chain and forms a dimer of immunoglobulin Fc fragments through an inter-disulfide bond.

In the present invention, the hinge sequence may be modified such that a part of the hinge sequence having the following amino acid sequence is deleted and thus there is only one cysteine residue in the sequence, but is not limited thereto:

(SEQ ID NO: 6)
Glu-Ser-Lys-Tyr-Gly-Pro-Pro-Cys-Pro-Ser-Cys-Pro

The hinge sequence may be one in which the 8th or 11th cysteine residue in the hinge sequence of SEQ ID NO: 6 is deleted and thus only one cysteine residue is included in the sequence. The hinge sequence of the present invention may consist of 3 to 12 amino acids, including only one cysteine residue, but the hinge sequence is not limited thereto. More specifically, the hinge sequence of the present invention may have the following sequences: Glu-Ser-Lys-Tyr-Gly-Pro-Pro-Pro-Ser-Cys-Pro (SEQ ID NO: 7), Glu-Ser-Lys-Tyr-Gly-Pro-Pro-Cys-Pro-Ser-Pro (SEQ ID NO: 8), Glu-Ser-Lys-Tyr-Gly-Pro-Pro-Cys-Pro-Ser (SEQ ID NO: 9), Glu-Ser-Lys-Tyr-Gly-Pro-Pro-Cys-Pro-Pro (SEQ ID NO: 10), Lys-Tyr-Gly-Pro-Pro-Cys-Pro-Ser (SEQ ID NO: 11), Glu-Ser-Lys-Tyr-Gly-Pro-Pro-Cys (SEQ ID NO: 12), Glu-Lys-Tyr-Gly-Pro-Pro-Cys (SEQ ID NO: 13), Glu-Ser-Pro-Ser-Cys-Pro (SEQ ID NO: 14), Glu-Pro-Ser-Cys-Pro (SEQ ID NO: 15), Pro-Ser-Cys-Pro (SEQ ID NO: 16), Glu-Ser-Lys-Tyr-Gly-Pro-Pro-Ser-Cys-Pro (SEQ ID NO: 17), Lys-Tyr-Gly-Pro-Pro-Pro-Ser-Cys-Pro (SEQ ID NO: 18), Glu-Ser-Lys-Tyr-Gly-Pro-Ser-Cys-Pro (SEQ ID NO: 19), Glu-Ser-Lys-Tyr-Gly-Pro-Pro-Cys (SEQ ID NO: 20), Lys-Tyr-Gly-Pro-Pro-Cys-Pro (SEQ ID NO: 21), Glu-Ser-Lys-Pro-Ser-Cys-Pro (SEQ ID NO: 22), Glu-Ser-Pro-Ser-Cys-Pro (SEQ ID NO: 23), Glu-Pro-Ser-Cys (SEQ ID NO: 24), Ser-Cys-Pro (SEQ ID NO: 25). More specifically, the hinge sequence may include the amino acid sequence of SEQ ID NO: 25 (Ser-Cys-Pro) or SEQ ID NO: 16 (Pro-Ser-Cys-Pro), but is not limited thereto.

The immunoglobulin Fc fragment of the present invention may be in a form in which two molecules of the immunoglobulin Fc chain form a dimer due to the presence of a hinge sequence therein, and in addition, the peptide conjugate of Chemical Formula 1 of the present invention may be in a form in which one end of the linker is linked to one chain of the dimeric immunoglobulin Fc fragments, but the immunoglobulin Fc fragment and the conjugate are not limited thereto.

As used herein, the term "N-terminus" refers to the amino terminus of a protein or polypeptide, and it may include 1, 2, 3, 4, 5, 6, 7, 8, 9, or 10 or more amino acids from the most terminal end or the most terminal end of the amino terminus. The immunoglobulin Fc fragment of the present invention may include a hinge sequence in the N-terminus, but is not limited thereto.

Additionally, the immunoglobulin Fc fragment of the present invention may be an extended Fc fragment, which includes all or part of the heavy chain constant region 1 (CH1) and/or light chain constant region 1 (CL1) excluding the heavy chain and light chain variable regions of an immunoglobulin, as long as it has substantially the equivalent or an improved effect compared to its native type. Additionally, the immunoglobulin Fc fragment of the present invention may be a region in which some fairly long amino acid sequences corresponding to CH2 and/or CH3 are removed.

For example, the immunoglobulin Fc fragment of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination of (i) one or two or more domains among a CH1 domain, a CH2 domain, a CH3 domain, and a CH4 domain and (ii) an immunoglobulin hinge region (or part of the hinge region); or 6) a dimer of each domain of the heavy chain constant region and a light chain constant region, but the immunoglobulin Fc region is not limited thereto.

Additionally, in one embodiment, the immunoglobulin Fc fragment may have a dimeric form, and one molecule of the peptide of General Formula 1 may be covalently linked to one Fc region in a dimeric form, in particular, the immunoglobulin Fc and the peptide of General Formula 1 may be covalently linked to each other through a polyethylene glycol linker. Meanwhile, it is also possible that two molecules of the peptide of General Formula 1 are symmetrically linked to one Fc region in a dimeric form. In particular, the immunoglobulin Fc and the peptide of General Formula 1 may be linked to each other through a polyethylene glycol linker, but is not limited to the embodiments described above.

In addition, the immunoglobulin Fc fragment of the present invention includes native amino acid sequences as well as sequence derivatives thereof. The amino acid sequence derivative means that the sequence is different the native amino acid sequence due to deletion, insertion, non-conservative or conservative substitution, or a combination thereof in one or more amino acid residues in the native amino acid sequence.

For example, amino acid residues at positions 214 to 238, 297 to 299, 318 to 322, or 327 to 331 in IgG Fc, which are known to be important for linkage, may be used as the sites suitable for variation.

Additionally, various types of derivatives are available, for example, one where the site capable of forming an inter-disulfide bond is removed; one where several N-terminal amino acids from native Fc are removed; or one where a methionine residue is added to the N-terminus of native Fc, etc. Additionally, complement binding sites (e.g., C1q binding sites) or antibody-dependent cell-mediated cytotoxicity (ADCC) sites may be removed to eliminate the effector function. The techniques for preparing the sequence derivatives of these immunoglobulin Fc fragments are disclosed in International Publication Nos. WO 97/34631, WO 96/32478, etc.

Amino acid substitutions in a protein or peptide that do not alter the entire activity of a molecule are well known in the art (H. Neurath, R. L. Hill, *The Proteins*, Academic Press, New York, 1979). The most common substitutions occur between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, amino acids may be modified by phosphorylation, sulfation, acrylation, glycosylation, methylation, farnesylation, acetylation, amidation, etc.

The Fc derivatives described above may be those which exhibit the same biological activity as the Fc fragment of the present invention and have an increased structural stability of the Fc fragment against heat, pH, etc.

Additionally, such an Fc fragment may be obtained from a native type isolated from humans or animals (e.g., cows, goats, pigs, mice, rabbits, hamsters, rats, guinea pigs, etc.) or may be recombinants or derivatives thereof obtained from transformed animal cells or microorganisms. In particular, the Fc region may be obtained from a native immunoglobulin by isolating a whole immunoglobulin from a living human or animal and treating the isolated immunoglobulin with protease. When the whole immunoglobulin is treated with papain, it is cleaved into Fab and Fc fragments, whereas when treated with pepsin, it is cleaved into pF'c and $F(ab)_2$ fragments. Fc or pF'c can be isolated using size exclusion chromatography, etc. In a more specific embodiment, the Fc fragment may be a human immunoglobulin Fc fragment where a human-derived Fc fragment is obtained from a microorganism.

Additionally, the immunoglobulin Fc fragment may be in the form of native glycans, increased or decreased glycans compared to the native type, or in a deglycosylated form. The increase, decrease, or removal of the immunoglobulin Fc glycans may be achieved by conventional methods such as a chemical method, enzymatic method, and genetic engineering method using a microorganism. In particular, the immunoglobulin Fc fragment where the glycans are removed from the Fc shows a significant decrease in binding affinity for the complement (C1q) and a decrease or removal of antibody-dependent cytotoxicity or complement-dependent cytotoxicity, and thus it does not induce unnecessary immune responses in vivo. In this regard, an immunoglobulin Fc fragment in a deglycosylated or aglycosylated form may be more suitable to meet the original object of the present invention as a drug carrier.

As used herein, the term "deglycosylation" refers to an Fc fragment in which glycans are removed with an enzyme, and the term "aglycosylation" refers to a non-glycosylated Fc fragment produced in prokaryotes, more specifically *E. coli.*

Meanwhile, the immunoglobulin Fc fragment may be derived from humans or animals (e.g., cows, goats, pigs, mice, rabbits, hamsters, rats, guinea pigs, etc.), and in a more specific embodiment, it may be derived from humans.

Additionally, the immunoglobulin Fc fragment may be derived from IgG, IgA, IgD, IgE, IgM, or a combination or hybrid thereof. In a more specific embodiment, the immunoglobulin Fc fragment may be derived from IgG or IgM, which are among the most abundant proteins in human blood, and in an even more specific embodiment, it may be derived from IgG, which is known to enhance the half-lives of ligand-binding proteins. In an even yet more specific embodiment, the immunoglobulin Fc fragment may be an IgG4 Fc fragment, and in the most specific embodiment, it may be an aglycosylated Fc fragment derived from a human IgG4, but is not limited thereto.

Additionally, in one embodiment, the immunoglobulin Fc fragment, being a human IgG4 Fc fragment, may be in the form of a homodimer in which two monomers are linked through an inter-disulfide bond (an inter-chain form) between cysteines, which are the $3^{rd}$ amino acid of each monomer. In particular, the homodimer may have two disulfide bonds (an intra-chain form), i.e., an intra-disulfide bond between the cysteines at positions 35 and 95 in one monomer and an internal disulfide bond between the cysteines at positions 141 and 199 in other monomer; and/or each monomer may consist of 221 amino acids, and the amino acids forming the homodimer may consist of a total of 442 amino acids, but the number of amino acids is not limited thereto. Specifically, the immunoglobulin Fc fragment may be one in which two monomers having the amino acid sequence of SEQ ID NO: 5 (consisting of 221 amino acids) form a homodimer through an inter-disulfide bond between cysteines, which are the $3^{rd}$ amino acid of each monomer, and in which the monomers of the homodimer independently form an intra-disulfide bond between the cysteines at positions 35 and 95 and an intra-disulfide bond between the cysteines at positions 141 and 199, but the immunoglobulin Fc fragment is not limited thereto. In one example, the immunoglobulin Fc fragment may be a homodimer including the amino acid sequence of SEQ ID NO: 26 (consisting of 442 amino acids), but is not limited thereto.

Meanwhile, as used herein, the term "combination" means that polypeptides encoding single-chain immunoglobulin Fc fragments of the same origin are linked to a single-chain polypeptide of a different origin to form a dimer or multimer.

That is, it is possible to prepare a dimer or multimer from two or more fragments selected from the group consisting of IgG Fc fragment, IgA Fc fragment, IgM Fc fragment, IgD Fc fragment, and IgE Fc fragment.

As used herein, the term "hybrid" means that sequences corresponding two or more immunoglobulin Fc fragments of different origins are present in a single chain of an immunoglobulin constant region. In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

Meanwhile, IgG may also be divided into the IgG1, IgG2, IgG3, and IgG4 subclasses, and the present invention may include combinations or hybrids thereof. Preferred are the IgG2 and IgG4 subclasses, and most preferred is the Fc fragment of IgG4, which rarely has effector functions such as complement-dependent cytotoxicity (CDC).

Another aspect for implementing the present invention provides a method for preparing a liquid formulation of a peptide conjugate of Chemical Formula 1, including: mixing (a) the peptide conjugate of Chemical Formula 1 with (b) i) a buffering agent, ii) a saccharide, and iii) a nonionic surfactant.

The conjugate, buffering agent, saccharide, nonionic surfactant, and liquid formulation are as described above.

Still another aspect of the present invention provides a pharmaceutical composition for preventing or treating obesity or diabetes, including the liquid formulation.

As used herein, the term "prevention" refers to all actions that inhibit or delay the development of a target disease. As used herein, the term "prevention" means administering the conjugate of the present invention to inhibit or delay the development of diabetic conditions, such as abnormal blood glucose levels or abnormal insulation secretion, or obesity conditions such as an increase in body weight or body fat.

As used herein, the term "treatment" refers to all actions that alleviate, ameliorate or relieve the symptoms of the disease developed. As used herein, the term "treatment" means administering the conjugate of the present invention to alleviate, ameliorate or relieve the above diabetic conditions or obesity conditions to normalize blood glucose levels and insulin secretion and reduce body weight or body fat.

As used herein, the term "obesity" refers to an excessive amount of fat tissue in the body. A body mass index (=weight (kg) divided by height (m)) of 25 or more is defined as obesity. Obesity generally results from an energy imbalance in which energy intake exceeds energy expenditure over time. Obesity is a metabolic disease that affects the entire body and highly likely to lead to diabetes and hyperlipidemia. In addition, obesity is related to sexual dysfunction, arthritis, and an increased risk of the development of cardiovascular diseases, and is also related to the development of cancer in some cases.

As used herein the term "diabetes" refers to a kind of metabolic disease in which insulin secretion is insufficient or normal functions are not made. Diabetes is characterized by hyperglycemia, which is an increased blood glucose level, thereby causing various symptoms, and thus, glucose is excreted with urine.

The pharmaceutical composition of the present invention may further include a pharmaceutically acceptable carrier, excipient or diluent. As used herein, the term "pharmaceutically acceptable" means an amount that is sufficient to exhibit therapeutic effects and causes no side effects. The dose of the active ingredient of the pharmaceutical composition of the present invention may be readily determined by those skilled in the art depending on the type of disease, the patient's age, weight, health condition, sex, and drug sensitivity, the route of administration, the mode of administration, the frequency of administration, the duration of treatment, drugs used in combination or coincident with the composition, and other factors known in the medical field.

Yet another aspect of the present invention provides a method for preventing or treating obesity or diabetes, including administering the liquid formulation to a subject.

The liquid formulation, obesity and diabetes are as described above.

As used herein, the term "subject" refers to a subject suspected of having obesity or diabetes, and means mammals, including humans, rats and domestic animals, which have or are at the risk of developing the above disease. However, the subject may be any subject that can be treated by the liquid formulation of the present invention.

The treatment method of the present invention may include administering the pharmaceutical composition including the liquid formulation in a pharmaceutically effective amount. An appropriate total daily dose may be determined within the scope of correct medical judgment by a practitioner, and may be administered once or several times in divided doses. However, for the purpose of the present invention, it is preferred that the specific therapeutically effective dose for any particular patient be applied differently depending on the kind and degree of responses to be achieved, specific compositions including whether other agents are occasionally used therewith, the patient's age, body weight, general health conditions, sex and diet, administration time, administration route, excretion rate of the composition, duration of treatment, various factors including drugs used in combination or simultaneously with the specific compositions, and similar factors well known in the medical field.

Hereinafter, the present invention will be described in more detail with reference to the following Examples. However, these Examples are for illustrative purposes only and the scope of the invention is not limited by these Examples.

Example 1: Preparation of GLP-1/Glucagon Receptor Dual Agonist

In order to measure the stability of the GLP-1/glucagon receptor dual agonist, which exhibits activities on both the GLP-1 receptor and the glucagon receptor, in the liquid formulation of the present invention, GLP-1/glucagon receptor dual agonists having the following amino acid sequences were synthesized (Table 1). In the present invention, the GLP-1/glucagon receptor dual agonist may be used interchangeably with an oxyntomodulin derivative.

TABLE 1

| SEQ ID NO: | Sequence | Note |
|---|---|---|
| SEQ ID NO: 2 | HAibQGTFTSDYSKYL DEKRAKEFVQWLMNTC | |

TABLE 1-continued

| SEQ ID NO: | Sequence | Note |
|---|---|---|
| SEQ ID NO: 3 | HAibQGTFTSDYSKYL D**E**KRA**K**EFVQWLMNTC | Ring formation |
| SEQ ID NO: 4 | HAibQGTFTSDYS**K**YL D**E**KRAKEFVQWLM**N**TC | Ring formation |

Amino acids indicated in bold in Table 1 mean that the amino acids indicated in bold form a ring with each other. In addition, Aib means aminoisobutyric acid, a non-natural amino acid.

Example 2: Preparation of Mono-PEGylated Immunoglobulin Fc Fragment

Example 2-1. Preparation of Mono-PEGylated Immunoglobulin Fc Fragment

In order to prepare a mono-PEGylated immunoglobulin Fc fragment having a structure in which one of the two N-terminus of the immunoglobulin Fc fragment is PEGylated, an immunoglobulin Fc region (49.8 kDa, homodimer of SEQ ID NO: 5) having a hinge region with a Pro-Ser-Cys-Pro sequence at the N-terminus was reacted with a PEG linker of Chemical Formula 2 (number average molecular weight of 10 kDa) in a molar ratio (immunoglobulin Fc region:PEG linker) of 1:1 with a concentration of 50 g/L of the immunoglobulin Fc region at 6° C.±4° C. for about 4 hours.

[Chemical Formula 2]

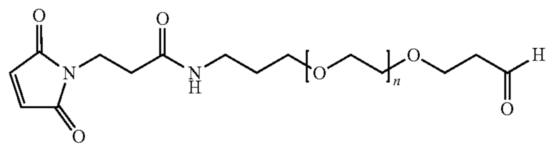

Specifically, the reaction was performed in a composition including a 5 mM Bis-Tris buffer (pH 6.5) and potassium phosphate, and 10 mM $NaCNBH_3$ (sodium cyanoborohydride) was added thereto as a reducing agent. In order to obtain a mono-PEGylated immunoglobulin Fc fragment, the reaction solution was diluted with the Bis-Tris buffer and purified.

Herein, the mono-PEGylated immunoglobulin Fc fragment was purified by a CAPTOQ IMPRES™ column (GE Healthcare, anion-exchange chromatography) using a buffer containing Bis-Tris and a sodium chloride concentration gradient.

Example 2-2. Analysis of Structure of Mono-PEGylated Immunoglobulin Fc Fragment The mono-PEGylated immunoglobulin Fc fragment prepared in Example 2-1 was structurally analyzed by MALDI-TOF and Peptide mapping. As a result of MALDI-TOF, the resultant was identical to an expected molecular weight of the mono-PEGylated immunoglobulin Fc fragment, and as a result of Peptide mapping, it was confirmed that over 90% of PEG was PEGylated at the N-terminus of the immunoglobulin Fc fragment.

Meanwhile, as a result of analyzing the mono-PEGylated immunoglobulin Fc fragment (Chemical Formula 3) prepared in Example 2-1 above using SE-HPLC, RP-HPLC, and IE-HPLC assays, the purity was confirmed to be 90% or more in SE-HPLC, 90% or more in RP-HPLC, and 80% or more in IE-HPLC.

[Chemical Formula 3]

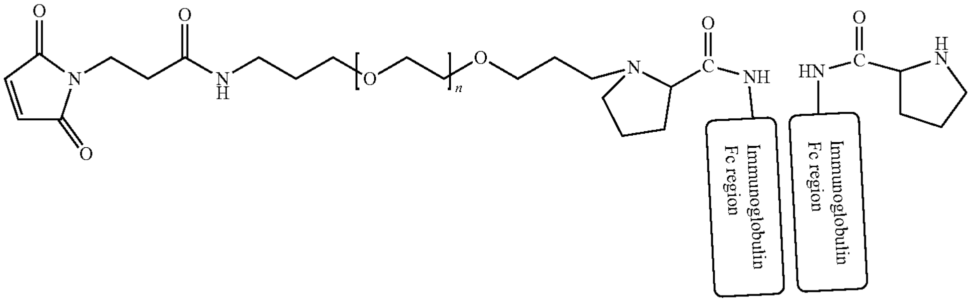

Example 3: Preparation of Conjugate by Linkage of PEGylated Immunoglobulin Fc Fragment to Oxyntomodulin Derivative A long-acting conjugate was prepared as follows by linking the mono-PEGylated immunoglobulin Fc fragment prepared in Example 2-1 to an oxyntomodulin derivative of SEQ ID NO: 3 (amidated at C-terminus) selected as a representative oxyntomodulin derivative.

The mono-PEGylated immunoglobulin Fc fragment was reacted with the oxyntomodulin derivative via peptide conjugation without performing ultrafiltration/diafiltration. Specifically, the long-acting conjugate (immunoglobulin Fc fragment-PEG-containing linker-oxyntomodulin derivative) was prepared via peptide conjugation of the oxyntomodulin derivative (SEQ ID NO: 3), which is a GLP-1/glucagon receptor dual agonist, after the anion-exchange chromatography of Example 2-1 without performing ultrafiltration/diafiltration. In the present invention, the term "long-acting conjugate" may be used interchangeably with "long-acting oxyntomodulin derivative conjugate".

Here, in order to link a maleimide reactive group at one terminus of PEG of the mono-PEGylated immunoglobulin Fc fragment to cysteine of the oxyntomodulin derivative, the mono-PEGylated immunoglobulin Fc fragment was reacted with the oxyntomodulin derivative in a molar ratio of 1:1 with an oxyntomodulin derivative protein concentration of 0.2 g/L at 6° C.±4° C. for about 2 hours. In particular, the reaction solution was maintained in a Tris-Cl buffer (6° C.±4° C.) including isopropanol. As a result of analyzing the resultant after reaction using SE-HPLC, RP-HPLC, and IE-HPLC assays, the purity of the immunoglobulin Fc fragment-PEG-containing linker-oxyntomodulin derivative conjugate (Chemical Formula 4) was confirmed to be 90% or more in SE-HPLC, 80% or more in RP-HPLC, and 80% or more in IE-HPLC.

Thereafter, the resultant of the reaction was subjected to hydrophobic interaction chromatography once using a SOURCE™ 15 ISO column (GE Healthcare). By-products were eliminated by this process, and the immunoglobulin Fc fragment-PEG-containing linker-oxyntomodulin derivative conjugate was obtained. Here, the conjugate was purified using a buffer containing sodium citrate and an ammonium sulfate concentration gradient.

The eluted immunoglobulin Fc fragment-PEG-containing linker-oxyntomodulin derivative conjugate (Chemical Formula 4) was analyzed by MALDI-TOF, SE-HPLC, RP-HPLC, and IE-HPLC assays. It was confirmed that the resultant was identical to an expected molecular weight of the immunoglobulin Fc fragment-PEG-containing linker-oxyntomodulin derivative conjugate based on the analysis results of MALDI-TOF. Also, it was confirmed that the conjugate was prepared in high purity of 90% or more in SE-HPLC, 90% or more in RP-HPLC, and 90% or more in IE-HPLC.

[Chemical Formula 4]

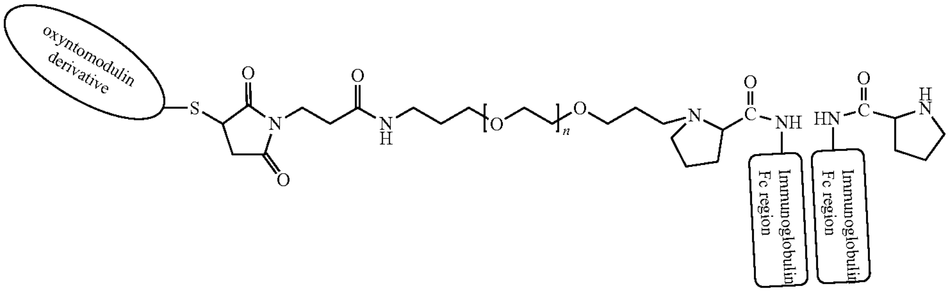

Example 4: Preparation of Liquid Formulations and Evaluation of Osmotic Pressure In order to confirm the stability of the liquid formulation, which is a newly prepared composition of the long-acting oxyntomodulin derivative conjugate prepared in Example 3, as a comparative example, a liquid formulation (Comparative Example) of the composition disclosed in International Publication No. WO 2014-073842 and the liquid formulation (Example) of the new composition according to the present invention were prepared according to the compositions shown in Table 2 below. For the formulation of Example, as representative examples of the buffering agent, saccharide and nonionic surfactant, which are the composition of the stabilizer of the present invention, acetic acid and a sodium salt thereof as the buffering agent, sucrose as the saccharide, and polysorbate 20 as the nonionic surfactant were selected.

The formulation of the Comparative Example, which is a conventional formulation, had a higher osmotic pressure than blood, and in addition, a new formulation was prepared to further improve stability. Mannitol was changed to sucrose while lowering the pH of the conventional formulation to improve stability. Accordingly, it was confirmed that the osmotic pressure was also reduced to a level similar to that of blood, and the presence or absence of methionine addition had no effect on stability, and thus was omitted in the Examples of the present invention. As a result of measuring osmotic pressure, the formulation of Comparative Example had an osmotic pressure of 494 mOsm/kg, and the formulation of Example had an osmotic pressure of 305 mOsm/kg, which was at a level similar to the osmotic pressure of blood (approximately 300 mOsm/kg).

TABLE 2

| | Buffering agent | Sugar alcohol or saccharide | Nonionic surfactant | Stabilizer | Peptide conjugate |
|---|---|---|---|---|---|
| Comparative Example | 20 mM citric acid-sodium citrate (pH 5.4) | 6% (w/v) mannitol | 0.02% (w/v) polysorbate 20 | 0.1 mg/mL methionine | 374 nmol/mL |
| Example | 10 mM acetic acid-sodium acetate (pH 5.1) | 8.5% (w/v) sucrose | 0.02% (w/v) polysorbate 20 | — | 374 nmol/mL |

Example 5: Long-Term Stability Evaluation of Liquid Formulation of Example

In order to confirm the long-term stability of the liquid formulation composition (Example) of the long-acting oxyntomodulin derivative conjugate prepared in Example 4, it was stored at 5° C.±3° C. for 0 to 12 months, and then the stability was analyzed using ion-exchange high-performance liquid chromatography (IE-HPLC), size-exclusion high-performance liquid chromatography (SE-HPLC), and reverse-phase high-performance liquid chromatography (RP-HPLC). In Tables 3, 4, and 5, IE-HPLC (%), RP-HPLC (%), and SE-HPLC (%) indicate the area % at each analysis point of the peak corresponding to the long-acting oxyntomodulin derivative conjugate.

TABLE 3

| | Long-term stability Evaluation (5° C. ± 3° C.) | | | | |
|---|---|---|---|---|---|
| IE-HPLC | 0 months | 1 month | 3 months | 6 months | 12 months |
| Example | 97.8 | 95.3 | 95.5 | 95.0 | 91.7 |

TABLE 4

| | Long-term stability Evaluation (5° C. ± 3° C.) | | | | |
|---|---|---|---|---|---|
| RP-HPLC | 0 months | 1 month | 3 months | 6 months | 12 months |
| Example | 95.7 | 94.9 | 95.8 | 93.7 | 93.9 |

TABLE 5

| | Long-term stability Evaluation (5° C. ± 3° C.) | | | | |
|---|---|---|---|---|---|
| SE-HPLC | 0 months | 1 month | 3 months | 6 months | 12 months |
| Example | 98.7 | 99.1 | 99.2 | 98.2 | 98.1 |

As can be seen from the above results, it was confirmed that the liquid formulation composition of the present invention had high stability up to 12 months, and thus it can be found that it is the optimal composition for long-term storage.

Example 6: Accelerated Stability Evaluation

In order to confirm the accelerated stability of the liquid formulation of the Example prepared in Example 4 and the liquid formulation of the Comparative Example, the liquid formulations were stored for 0 to 6 months at 25° C.±2° C. and 60%±5% relative humidity, and then the stability was analyzed using IE-HPLC, RP-HPLC, and SE-HPLC. Accelerated stability test is a test designed to increase chemical degradation or physical change of drug substance or drug product by adopting excessive storage conditions. In addition to the long-term stability test, the accelerated stability test evaluates chemical effects over a long period under non-accelerated conditions through accelerated stability evaluation and can evaluate the effects when conditions diverge from the indicated storage conditions for a short period of time, such as situations that may occur during transport. In Tables 6, 7, and 8, IE-HPLC (%), RP-HPLC (%), and SE-HPLC (%) indicate the area % at each analysis point of the peak corresponding to the long-acting oxyntomodulin derivative conjugate.

TABLE 6

| | Accelerated Conditions (25° C. ± 2° C./60% ± 5%) | | | |
|---|---|---|---|---|
| IE-HPLC | 0 months | 1 month | 3 months | 6 months |
| Comparative Example | 97.6 | 90.6 | 75.1 | 57.0 |
| Example | 97.8 | 92.4 | 79.8 | 64.8 |

TABLE 7

| | Accelerated Conditions (25° C. ± 2° C./60% ± 5%) | | | |
|---|---|---|---|---|
| RP-HPLC | 0 months | 1 month | 3 months | 6 months |
| Comparative Example | 95.5 | 94.5 | 94.2 | 89.7 |
| Example | 95.7 | 94.9 | 94.5 | 91.6 |

TABLE 8

| | Accelerated Conditions (25° C. ± 2° C./60% ± 5%) | | | |
|---|---|---|---|---|
| SE-HPLC | 0 months | 1 month | 3 months | 6 months |
| Comparative Example | 98.6 | 98.1 | 96.2 | 91.0 |
| Example | 98.7 | 98.3 | 97.0 | 92.5 |

As can be seen from the results of Tables 6, 7, and 8, it was confirmed that the composition of the liquid formulation, in which the sugar alcohol of the present invention was absent and sucrose, a saccharide, was present, showed high stability under accelerated conditions up to 6 months compared to the Comparative Example. These results suggest that the liquid formulation composition of the present invention has high stability.

Example 7: Stress Stability Evaluation

In order to confirm the stress stability of the liquid formulation (Example) of the long-acting oxyntomodulin derivative conjugate prepared in Example 4, it was stored from 0 to 4 weeks under the conditions of 40° C.±2° C. and 75%±5% relative humidity, and the appearance was analyzed separately from the liquid formulation of the Comparative Example.

The stress stability test is a test to determine the effect of the change in conditions on the product when the product is exposed to conditions other than the applied storage conditions, and to identify the degradation pattern and physicochemical stability of the drug substance and/or drug product. Table 9 shows the appearance of the liquid formulations of the Comparative Example and the Example under the stress conditions.

TABLE 9

| | Stress Conditions (40° C. ± 2° C./75% ± 5%) | | | | |
|---|---|---|---|---|---|
| Appearance | 0 weeks | 1 week | 2 weeks | 3 weeks | 4 weeks |
| Comparative Example | Transparent | Slightly opaque | Slightly opaque | Precipitated | Precipitated |
| Example | Transparent | Transparent | Transparent | Transparent | Transparent |

As can be seen from the results in Table 9, in the case of the liquid formulation composition of the Comparative Example under stress conditions, the appearance of the long-acting oxyntomodulin derivative conjugate became opaque from 1 week, and precipitation occurred at 3 weeks; in contrast, the composition of the Example, which is a composition of the liquid formulation in which the sugar alcohol of the present invention was absent and sucrose, a saccharide, was present, maintained a transparent appearance even until 4 weeks, confirming that the long-acting oxyntomodulin derivative conjugate, which is the target for stabilization, is stable without precipitation. These results suggest that the liquid formulation composition of the present invention has higher stability than the known composition, and thus can be provided as a liquid formulation of pharmaceuticals.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A liquid formulation for stabilizing a long-acting glucagon-like peptide-1 (GLP-1)/glucagon receptor dual agonist peptide conjugate of Chemical Formula 1, the liquid formulation comprising:

18 nmol/mL to 940 nmol/mL of the long-acting GLP-1/glucagon receptor dual agonist peptide conjugate of Chemical Formula 1, 5 mM to 25 mM of acetic acid or a salt thereof in an amount for maintaining a pH of the liquid formulation in a range of 4.8 to 5.5, 4% w/v to 10% w/v of sucrose, and 0.01% w/v to 0.1% w/v of a nonionic surfactant selected from poloxamer, polysorbate, or a combination thereof;

[Chemical Formula 1]

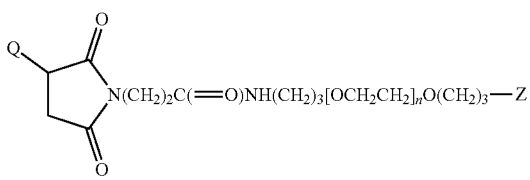

wherein Q is a peptide comprising the amino acid sequence set forth in SEQ ID NOS: 2, 3, or 4;

Z is an immunoglobulin Fc fragment; and n is a natural number, wherein the value of n is determined such that the average molecular weight of the $[OCH_2CH_2]_n$ region in the peptide conjugate is 10 kDa.

2. The liquid formulation of claim 1, wherein the liquid formulation does not contain a sugar alcohol.

3. The liquid formulation of claim 1, wherein Q is the amino acid sequence of SEQ ID NO: 3.

4. The liquid formulation of claim 1, wherein Q is amidated at the C-terminus thereof.

5. The liquid formulation of claim 1, wherein Q is linked via a sulfur atom of cysteine.

6. The liquid formulation of claim 1, wherein the immunoglobulin Fc fragment is IgG4 Fc fragment.

7. The liquid formulation of claim 1, wherein Z is a dimer structure in which two immunoglobulin Fc fragment polypeptide chains are linked by a disulfide bond, and one N-terminus of the two immunoglobulin Fc fragments is linked through a nitrogen atom.

8. The liquid formulation of claim 1, wherein Z is a homodimer comprising two monomers, each monomer the amino acid sequence of SEQ ID NO: 5.

9. The liquid formulation of claim 8, wherein Z is linked via a nitrogen atom of proline at the N-terminus of one of the two monomers.

10. The liquid formulation of claim 1, wherein the immunoglobulin Fc fragment and Q are non-glycosylated.

11. The liquid formulation of claim 1, wherein the pH of the liquid formulation is 4.9 to 5.3.

12. The liquid formulation of claim 11, wherein the pH of the liquid formulation is 5.0 to 5.2.

13. The liquid formulation of claim 1, wherein the nonionic surfactant is selected from the group consisting of poloxamer 188, polysorbate 20, polysorbate 40, polysorbate 60, polysorbate 80, and a combination thereof.

14. The liquid formulation of claim 1, wherein the liquid formulation further comprises a stabilizer selected from the group consisting of arginine, glycine, methionine, and a combination thereof.

15. The liquid formulation of claim 8, wherein the liquid formulation comprises:

274 nmol/mL to 474 nmol/mL of the long-acting GLP-1/glucagon receptor dual agonist peptide conjugate of Chemical Formula 1, in which Q having an amidated C-terminus is linked via a sulfur atom of cysteine;

5 mM to 25 mM of acetic acid or a salt thereof in an amount for maintaining the pH of the liquid formulation in the range of 4.9 to 5.3

8.5% w/v of sucrose, and 0.02% w/v of polysorbate 20.

16. The liquid formulation of claim 15, wherein the liquid formulation has a transparent appearance when stored for one week under harsh test conditions of 40° C.±2° C. and relative humidity of 75%±5%.

17. The liquid formulation of claim 1, wherein the immunoglobulin Fc fragment is linked by a disulfide bond to another immunoglobulin Fc fragment to form a homodimer.

* * * * *

SEQUENCE LISTING

```
<160> NUMBER OF SEQ ID NOS: 26

<210> SEQ ID NO 1
<211> LENGTH: 30
<212> TYPE: PRT
<213> ORGANISM: Artificial Sequence
<220> FEATURE:
```

-continued

<223> OTHER INFORMATION: Formula 1 of oxyntomodulin derivative
<220> FEATURE:
<221> NAME/KEY: VARIANT
<222> LOCATION: (2)
<223> OTHER INFORMATION: Xaa = 2-aminoisobutyric acid
<220> FEATURE:
<221> NAME/KEY: VARIANT
<222> LOCATION: (12)
<223> OTHER INFORMATION: Xaa = Lysine
<220> FEATURE:
<221> NAME/KEY: VARIANT
<222> LOCATION: (16)
<223> OTHER INFORMATION: Xaa = glutamic acid
<220> FEATURE:
<221> NAME/KEY: VARIANT
<222> LOCATION: (20)
<223> OTHER INFORMATION: Xaa = Lysine

<400> SEQUENCE: 1

```
His Xaa Gln Gly Thr Phe Thr Ser Asp Tyr Ser Xaa Tyr Leu Asp Xaa
1               5                   10                  15

Lys Arg Ala Xaa Glu Phe Val Gln Trp Leu Met Asn Thr Cys
            20                  25                  30
```

<210> SEQ ID NO 2
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = 2-aminoisobutyric acid

<400> SEQUENCE: 2

```
His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = 2-aminoisobutyric acid
<220> FEATURE:
<221> NAME/KEY: VARIANT
<222> LOCATION: (16)..(20)
<223> OTHER INFORMATION: amino acids at position 16 and position 20 form a ring

<400> SEQUENCE: 3

```
His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: oxyntomodulin derivative
<220> FEATURE:

-continued

```
<221> NAME/KEY: VARIANT
<222> LOCATION: (2)
<223> OTHER INFORMATION: Xaa = 2-aminoisobutyric acid
<220> FEATURE:
<221> NAME/KEY: VARIANT
<222> LOCATION: (12)..(16)
<223> OTHER INFORMATION: amino acids at position 12 and position 16 form
      a ring

<400> SEQUENCE: 4

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 5
<211> LENGTH: 221
<212> TYPE: PRT
<213> ORGANISM: homo sapiens

<400> SEQUENCE: 5

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220


<210> SEQ ID NO 6
<211> LENGTH: 12
<212> TYPE: PRT
<213> ORGANISM: homo sapiens

<400> SEQUENCE: 6

Glu Ser Lys Tyr Gly Pro Pro Cys Pro Ser Cys Pro
1               5                   10
```

-continued

<210> SEQ ID NO 7
<211> LENGTH: 11
<212> TYPE: PRT
<213> ORGANISM: Artificial Sequence
<220> FEATURE:
<223> OTHER INFORMATION: Variant of hinge region

<400> SEQUENCE: 7

Glu Ser Lys Tyr Gly Pro Pro Pro Ser Cys Pro
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Variant of hinge region

<400> SEQUENCE: 8

Glu Ser Lys Tyr Gly Pro Pro Cys Pro Ser Pro
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Variant of hinge region

<400> SEQUENCE: 9

Glu Ser Lys Tyr Gly Pro Pro Cys Pro Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Variant of hinge region

<400> SEQUENCE: 10

Glu Ser Lys Tyr Gly Pro Pro Cys Pro Pro
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Variant of hinge region

<400> SEQUENCE: 11

Lys Tyr Gly Pro Pro Cys Pro Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Variant of hinge region

<400> SEQUENCE: 12

Glu Ser Lys Tyr Gly Pro Pro Cys
1               5

<210> SEQ ID NO 13

<211> LENGTH: 7
<212> TYPE: PRT
<213> ORGANISM: Artificial Sequence
<220> FEATURE:
<223> OTHER INFORMATION: Variant of hinge region

<400> SEQUENCE: 13

Glu Lys Tyr Gly Pro Pro Cys
1 5

<210> SEQ ID NO 14
<211> LENGTH: 6
<212> TYPE: PRT
<213> ORGANISM: Artificial Sequence
<220> FEATURE:
<223> OTHER INFORMATION: Variant of hinge region

<400> SEQUENCE: 14

Glu Ser Pro Ser Cys Pro
1 5

<210> SEQ ID NO 15
<211> LENGTH: 5
<212> TYPE: PRT
<213> ORGANISM: Artificial Sequence
<220> FEATURE:
<223> OTHER INFORMATION: Variant of hinge region

<400> SEQUENCE: 15

Glu Pro Ser Cys Pro
1 5

<210> SEQ ID NO 16
<211> LENGTH: 4
<212> TYPE: PRT
<213> ORGANISM: Artificial Sequence
<220> FEATURE:
<223> OTHER INFORMATION: Variant of hinge region

<400> SEQUENCE: 16

Pro Ser Cys Pro
1

<210> SEQ ID NO 17
<211> LENGTH: 10
<212> TYPE: PRT
<213> ORGANISM: Artificial Sequence
<220> FEATURE:
<223> OTHER INFORMATION: Variant of hinge region

<400> SEQUENCE: 17

Glu Ser Lys Tyr Gly Pro Pro Ser Cys Pro
1 5 10

<210> SEQ ID NO 18
<211> LENGTH: 9
<212> TYPE: PRT
<213> ORGANISM: Artificial Sequence
<220> FEATURE:
<223> OTHER INFORMATION: Variant of hinge region

<400> SEQUENCE: 18

Lys Tyr Gly Pro Pro Pro Ser Cys Pro
1 5

<210> SEQ ID NO 19
<211> LENGTH: 9

<212> TYPE: PRT
<213> ORGANISM: Artificial Sequence
<220> FEATURE:
<223> OTHER INFORMATION: Variant of hinge region

<400> SEQUENCE: 19

Glu Ser Lys Tyr Gly Pro Ser Cys Pro
1 5

<210> SEQ ID NO 20
<211> LENGTH: 8
<212> TYPE: PRT
<213> ORGANISM: Artificial Sequence
<220> FEATURE:
<223> OTHER INFORMATION: Variant of hinge region

<400> SEQUENCE: 20

Glu Ser Lys Tyr Gly Pro Pro Cys
1 5

<210> SEQ ID NO 21
<211> LENGTH: 7
<212> TYPE: PRT
<213> ORGANISM: Artificial Sequence
<220> FEATURE:
<223> OTHER INFORMATION: Variant of hinge region

<400> SEQUENCE: 21

Lys Tyr Gly Pro Pro Cys Pro
1 5

<210> SEQ ID NO 22
<211> LENGTH: 7
<212> TYPE: PRT
<213> ORGANISM: Artificial Sequence
<220> FEATURE:
<223> OTHER INFORMATION: Variant of hinge region

<400> SEQUENCE: 22

Glu Ser Lys Pro Ser Cys Pro
1 5

<210> SEQ ID NO 23
<211> LENGTH: 6
<212> TYPE: PRT
<213> ORGANISM: Artificial Sequence
<220> FEATURE:
<223> OTHER INFORMATION: Variant of hinge region

<400> SEQUENCE: 23

Glu Ser Pro Ser Cys Pro
1 5

<210> SEQ ID NO 24
<211> LENGTH: 4
<212> TYPE: PRT
<213> ORGANISM: Artificial Sequence
<220> FEATURE:
<223> OTHER INFORMATION: Variant of hinge region

<400> SEQUENCE: 24

Glu Pro Ser Cys
1

<210> SEQ ID NO 25
<211> LENGTH: 3
<212> TYPE: PRT

```
<213> ORGANISM: Artificial Sequence
<220> FEATURE:
<223> OTHER INFORMATION: Variant of hinge region

<400> SEQUENCE: 25

Ser Cys Pro
1


<210> SEQ ID NO 26
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human
      Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one
      monomer
<220> FEATURE:
<221> NAME/KEY: MISC_FEATURE
<222> LOCATION: (222)..(442)
<223> OTHER INFORMATION: Amino acids at position 222 to 442 form one
      monomer
<220> FEATURE:
<221> NAME/KEY: DISULFID
<222> LOCATION: (3)..(224)
<223> OTHER INFORMATION: Amino acids at position 3 and position 224 form
      an inter-disulfide bond
<220> FEATURE:
<221> NAME/KEY: DISULFID
<222> LOCATION: (35)..(95)
<223> OTHER INFORMATION: Amino acids at position 35 and position 95 form
      an intra-chain disulfide bond
<220> FEATURE:
<221> NAME/KEY: DISULFID
<222> LOCATION: (141)..(199)
<223> OTHER INFORMATION: Amino acids at position 141 and position 199
      form an intra-chain disulfide bond
<220> FEATURE:
<221> NAME/KEY: DISULFID
<222> LOCATION: (256)..(316)
<223> OTHER INFORMATION: Amino acids at position 256 and position 316
      form an intra-chain disulfide bond
<220> FEATURE:
<221> NAME/KEY: DISULFID
<222> LOCATION: (362)..(420)
<223> OTHER INFORMATION: Amino acids at position 362 and position 420
      form an intra-chain disulfide bond

<400> SEQUENCE: 26

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80
```

-continued

```
Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```